United States Patent
Ramakrishnan

(10) Patent No.: US 7,555,390 B2
(45) Date of Patent: Jun. 30, 2009

(54) PETROPHYSICAL INTERPRETATION OF MULTIPASS ARRAY RESISTIVITY DATA OBTAINED WHILE DRILLING

(75) Inventor: Terizhandur S. Ramakrishnan, Boxborough, MA (US)

(73) Assignee: Schlumberger Technology Corporation, Cambridge, MA (US)

( * ) Notice: Subject to any disclaimer, the term of this patent is extended or adjusted under 35 U.S.C. 154(b) by 0 days.

(21) Appl. No.: 11/854,320

(22) Filed: Sep. 12, 2007

(65) Prior Publication Data

US 2008/0215242 A1    Sep. 4, 2008

Related U.S. Application Data

(60) Provisional application No. 60/892,274, filed on Mar. 1, 2007.

(51) Int. Cl.
G01V 1/40 (2006.01)
E21B 49/00 (2006.01)

(52) U.S. Cl. ............... 702/7; 166/252.2; 73/152.08

(58) Field of Classification Search ............... 702/7, 702/1, 2, 6, 9, 11, 12, 13; 324/324, 347, 324/353, 375; 166/252.1, 252.2; 73/152.06, 73/152.18, 152.08; 367/73; 703/5, 10
See application file for complete search history.

(56) References Cited

U.S. PATENT DOCUMENTS

| | | | |
|---|---|---|---|
| 3,929,011 A | * | 12/1975 | Jones ............... 73/152.41 |
| 5,463,549 A | | 10/1995 | Dussan et al. |
| 5,497,321 A | * | 3/1996 | Ramakrishnan et al. ....... 702/12 |
| 5,594,343 A | | 1/1997 | Clark et al. |
| 6,088,656 A | * | 7/2000 | Ramakrishnan et al. ....... 702/13 |
| 6,167,348 A | * | 12/2000 | Cannon ..................... 702/13 |
| 6,886,632 B2 | * | 5/2005 | Raghuraman et al. .... 166/252.4 |
| 7,324,898 B2 | | 1/2008 | Frenkel |

OTHER PUBLICATIONS

Bonner et al., Resistivity While Drilling-Images from the String, Oilfield Review, Spring 1996, pp. 4-19.
Ramakrishnan et al., Effect of Capillary Number on the Relative Permeability Function for Two-Phase Flow in Porous Media, Powder Technology, 1986, vol. 48, pp. 99-124.
Ramakrishnan et al., Water Cut and Fractional Flow Logs from Array Induction Measurements, SPE 36503, 1996, pp. 83-98.

* cited by examiner

Primary Examiner—Michael P. Nghiem
Assistant Examiner—Toan M Le
(74) Attorney, Agent, or Firm—Jody Lynn DeStefanis; Vincent Loccisano; James McAleenan

(57) ABSTRACT

Resistivity measurements at different radial depths of investigation obtained from time lapse resistivity data gained from multiple passes of a resistivity tool through a borehole are analyzed together to obtain indications of at least one of fractional flow, residual oil and water saturations, oil saturation, and water saturation in a formation. For each of the logging passes having resistivity measurements with multiple radial depths of investigation, filtrate loss into the formation is also obtained through joint inversion.

21 Claims, 7 Drawing Sheets

PETROPHYSICAL INTERPRETATION OF MULTIPASS ARRAY RESISTIVITY DATA OBTAINED WHILE DRILLING

CROSS-REFERENCE TO RELATED APPLICATIONS

This application claims benefits from U.S. Provisional Patent application No. 60/892,274 filed Mar. 1, 2007, now expired, the contents of which are hereby incorporated herein by reference. The present invention is related to co-owned U.S. Pat. No. 5,497,321, which is hereby incorporated by reference herein in its entirety.

BACKGROUND OF THE INVENTION

1. Field of the Invention

The present invention relates to investigation of earth formations. More particularly, the present invention relates to using resistivity measurements obtained during a plurality of passes of a resistivity tool in a borehole in order to obtain fractional flow characteristics of an earth formation. For purposes herein in both the specification and claims, the term "resistivity" is to be understood in its broadest sense to encompass the inverse thereof which is known as "conductivity".

2. State of the Art

U.S. Pat. No. 5,497,321 describes methods of providing a log of fractional flow characteristics of formations surrounding an earth borehole. According to the methods, a logging tool is suspended in a borehole and resistivity measurements with different radial depths of investigation (e.g., ten inches, twenty inches, thirty inches, sixty inches and ninety inches into the formation) are made while the logging tool is moved through the borehole, thereby obtaining resistivity logs at different radial depths. Using a formation conductivity model, simulated resistivity log values are generated from estimated values of fractional flow parameters. The simulated resistivity log values are compared with measured values from the logging tool in order to obtain and error indication. The values for the fractional flow parameters are modified accordingly. An iterative procedure is used to find best fit values, from which an output of formation fractional flow characteristics is produced. An output of the filtrate loss is also produced.

The methods of U.S. Pat. No. 5,497,321 have proven very useful in providing good answer products. However, because the resistivity measurements utilized in the methods are from a single pass of a borehole tool which is usually run after drilling is complete, the answer products can be influenced by mud filtrate which has entered into the formation. As will be appreciated by those skilled in the art, because the salinity of the mud filtrate can differ significantly from the salinity of the formation fluids, and because a water-based mud-filtrate changes the water saturation in an oil zone around the borehole, the resistivity measurements made in an invaded formation can be affected.

In order to minimize the effects of invasion on measurements, resistivity logging-while-drilling (LWD) tools have been introduced. One such tool is the Compensated Dual Resistivity (CDR—a trademark of Schlumberger) tool which provides a borehole compensated resistivity with two depths of investigation. Another such tool is the Array Resistivity Compensated (ARC5—a trademark of Schlumberger) tool, which is an array resistivity tool. The ARC5 tool is an LWD tool which transmits electromagnetic waves which induce an eddy current in the formation and measures signals from the formation. These tools operate at about 2 MHz which is a higher frequency than a typical wireline tool. The ARC5 has three transmitters above and two transmitters below the receiver array. It measures five attenuation and five phase-shift values. Borehole compensation is achieved by using a linear mix of three different transmitters; the choice of the three depending on the transmitter spacing for which the correction is desired. Resistivity measurements are generated for depths of investigation into the formation of 10, 16, 22, 28, and 34 inches, and may be plotted as logs. LWD tools such as the CDR and ARC5 have the advantage over conventional resistivity measurement tools in that the resistivity measurement is made before significant filtrate invasion has taken place.

SUMMARY OF THE INVENTION

The present invention provides methods, systems and apparatus capable of providing petrophysical interpretation from time lapse resistivity data gained from multiple passes of a resistivity tool through a formation.

The present invention also provides methods, systems, and apparatus for generating fractional flow information of a formation utilizing resistivity data.

The present invention further provides methods, systems, and apparatus for generating time-related filtrate loss information through the use of multiple pass resistivity data.

According to one aspect of the invention, LWD tools are regularly "tripped" out of the borehole in order to replace the drilling bit, and each time the LWD tool is tripped out of the borehole, resistivity information radially into the formation can be obtained along the length of the borehole. The resistivity information for a later trip will typically cover the entire previously investigated length of the borehole (from an earlier trip) as well as the most recently drilled portion of the borehole. However, because of a time lapse between the trips, additional filtrate may have entered the formation at various locations of the borehole which could affect the resistivity measurements. Methods, systems, and apparatus are provided for addressing petrophysical interpretation of such time-lapse data in a cohesive and consistent manner.

According to another aspect of the present invention, methods, systems and apparatus are provided wherein data obtained from a resistivity tool making multiple passes through the borehole may be utilized and jointly inverted. The combination of information from multiple passes, if analyzed with common fluid flow physics, increases the amount of data in relation to the number of unknowns, thereby resulting in improved quality of inversion.

In accordance with yet another aspect of this invention, one or more interpretation answer products may be provided. These one or more answer products may include, but are not limited to: (i) multiphase mobility as a function of saturation, (ii) filtrate lost at each stage of the acquisition of resistivity data, (iii) porosity partitioning in terms of movable and residual saturations and (iv) a radial resistivity profile at various stages of invasion that may be used to find formation resistivity in the invaded and uninvaded regions.

According to one embodiment of the invention, multiple resistivity measurements at different radial depths of investigation obtained from multiple passes through a borehole are analyzed by: (a) generating starting estimates of residual oil saturation $S_{or}$ and connate water saturation $S_{wc}$ for a given borehole depth, (b) utilizing the starting estimates and the measured resistivities, conducting an initial global multidimensional search for estimated values of residual water saturation $S_{wr}$ and filtrate loss quantities $Q_i$, i=1, . . . N for each borehole depth of the formation for which resistivity information was obtained over multiple (N) passes, and (c) using the starting estimates of residual oil saturation $S_{or}$ and connate water saturation $S_{wc}$ for a given borehole depth, the estimated values of residual water saturation $S_{wr}$ and filtrate loss quantities $Q_i$, i=1, ... N for each borehole depth resulting from the initial multidimensional search, and a flow model relating parameters such as $S_{wr}$, $S_{wc}$, $S_{orm}$ and $Q_i$ to resistivity at different radial depths into the formation, (i) comparing resistivity estimates output by the flow model to the resistivity measurements, and (ii) iteratively modifying one or more of the parameters and comparing the resulting estimates to the actual measurements to make determinations for one or more of the parameters. The determinations are then displayed as a log over borehole depth, or in another desired manner.

According to one embodiment of the invention, the initial multidimensional search is conducted utilizing a simplified flow model where fractional flow curves are reduced to straight lines.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
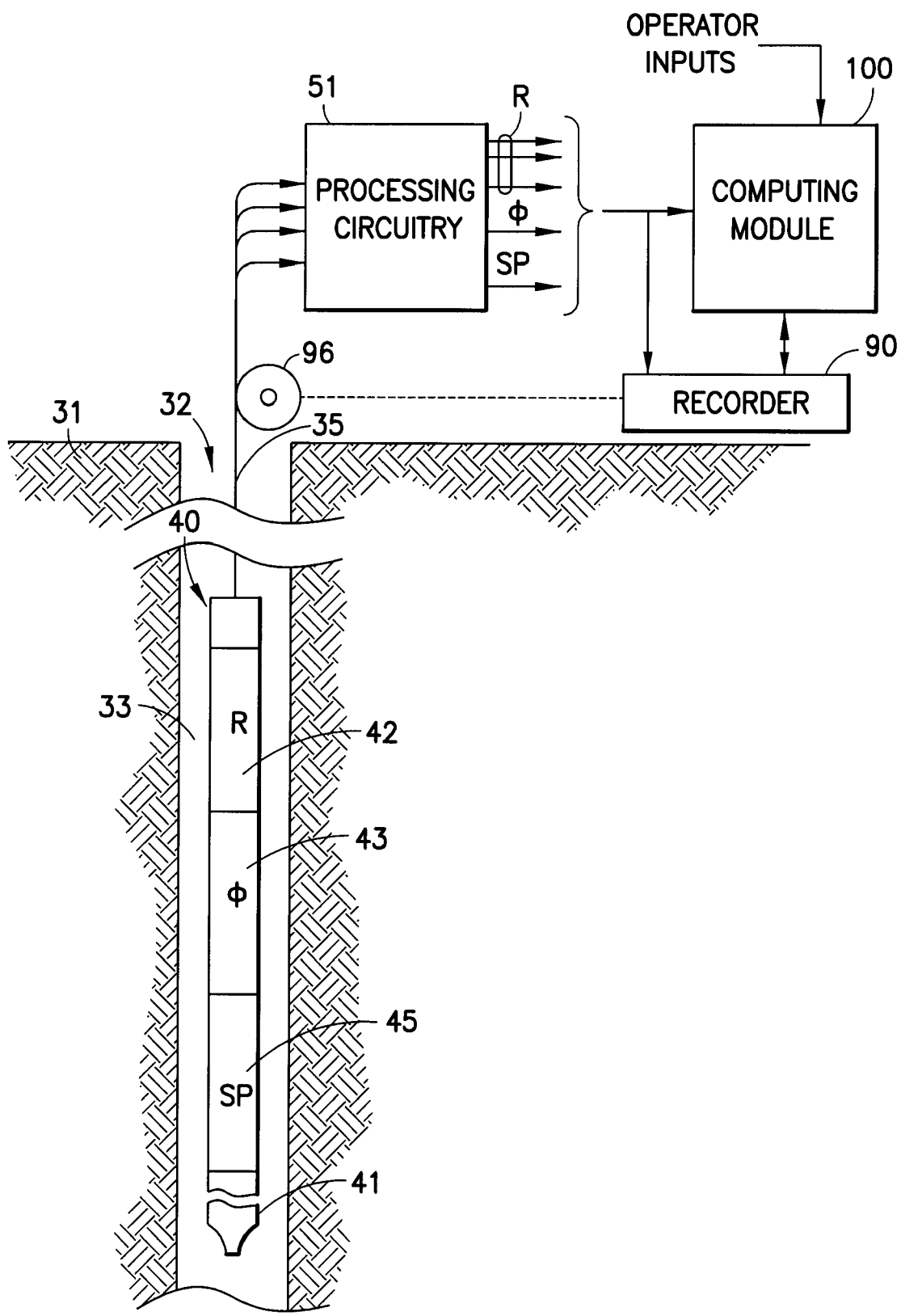
FIG. 1 is a schematic diagram, partially in block form, of equipment that can be utilized in practicing an embodiment of the invention.

Turning now to FIG. 1, an apparatus or system 10 is shown which can be used to practice an embodiment of the invention for investigation of earth formations 31 traversed by a borehole 32, which is filled with a drilling fluid 33. The investigating apparatus or system is shown to include a drill string 40 located in the borehole 32 as well as processing circuitry 51, shown at the surface, although portions thereof may be downhole. The apparatus or system 10 conventionally determines the depth (distance) of the drill string 40, and signals therefrom are coupled with a recorder 90 which generically represents known graphical, electrical, and/or other storage and recording functions performed on signals received from processing circuitry 51 and from a computing module 100. The computing module 100, which in the illustrated embodiment receives inputs from the processing circuitry 51, can be implemented, for example, by a suitably programmed general purpose computer. It will be understood, however, that a suitable special purpose digital or analog computer, which performs functions as described herein, could alternatively be employed.

The drill string 40 includes a drill 41 as well as a number of tools. In the present embodiment, the reference numeral 42 represents one or more logging-while drilling (LWD) (hereinafter referred to broadly as "logging") resistivity tools which collectively include the capability of measuring resistivity or conductivity (resistivity being the inverse of conductivity) at several radial depths of investigation and, preferably, at least five radial depths of investigation. It is well known in the art that one or more resistivity logging devices can be employed for this purpose. A single device which obtains measurements at several radial depths of investigation is the Array Resistivity Compensated Tool or ARC5 (a trademark of Schlumberger) tool, which derives from multiple receiver data five resistivity values at radial distances (depths) of generally 10", 16" 22", 28" and 34" from the borehole. Details of the ARC5 tool may be seen in U.S. Pat. No. 5,594,343 and S. Bonner et al., "Resistivity while drilling—Images from the string", *Oilfield Review*, Spring 1996. A further resistivity logging device that can, for example be utilized in conjunction with the ARC5 is the LWD-RAB (a trademark of Schlumberger) tool which measures resistivity at the drill bit. It will be understood that other resistivity logging device(s) can alternatively be employed.

The drill string 40 also includes, in this embodiment, a logging device 43 which is used to obtain measurements of porosity, $\Phi$. This logging tool may comprise, for example, a conventional type of nuclear (density/neutron) LWD device or a conventional type of acoustic LWD device or an NMR LWD device. Optionally further included in the tool string of this embodiment is a spontaneous potential ("SP") LWD device 45 which can be used in deriving an indication of the conductivity of connate formation water in the uninvaded zone. The tool string can also typically include appropriate conventional telemetry equipment and power supplies (not separately shown), as well as other logging subassemblies conventionally used with equipment of this type. It will also be understood that at least some of the measurements hereof could be made by wireline equipment. For example, after drilling is completed, a wireline tool such as the Microspherically Focused Log Tool or MSFL (a trademark of Schlumberger) or the Microcylindrically Focused Log Tool or MCFL (a trademark of Schlumberger) can be used to obtain resistivity data with a radial depth of investigation of a few inches (e.g., 1 inch to 4 inches) into the formation. Similarly, an Array Induction Tool or AIT (a trademark of Schlumberger) could be used as a wireline tool to provide information after drilling is completed. The AIT has characteristic depths of investigation of 10, 20, 30, 60 and 90 inches. Conventional density/neutron tools or NMR devices may be used to measure porosity and sampling devices may be used to derive formation water resistivity.

Because the drill string 40 will be tripped in and out of the borehole several times during the drilling of the borehole, it will be appreciated the ARC5 tool will be able to collect data during each pass of the drill string. Each time data is collected for a particular borehole location, the data will be time lapsed relative to earlier data collected for the same location. Because the borehole mud will have had time to infiltrate deeper (radially) into the formation, the resistivity data collected for a later pass will typically change relative to resistivity data collected for an earlier pass. However, as set forth hereinafter, if cleverly analysed, the extra data collected increases the amount of data in relation to the number of unknowns, thereby permitting a better determination of formation flow parameters.

Figure 2:
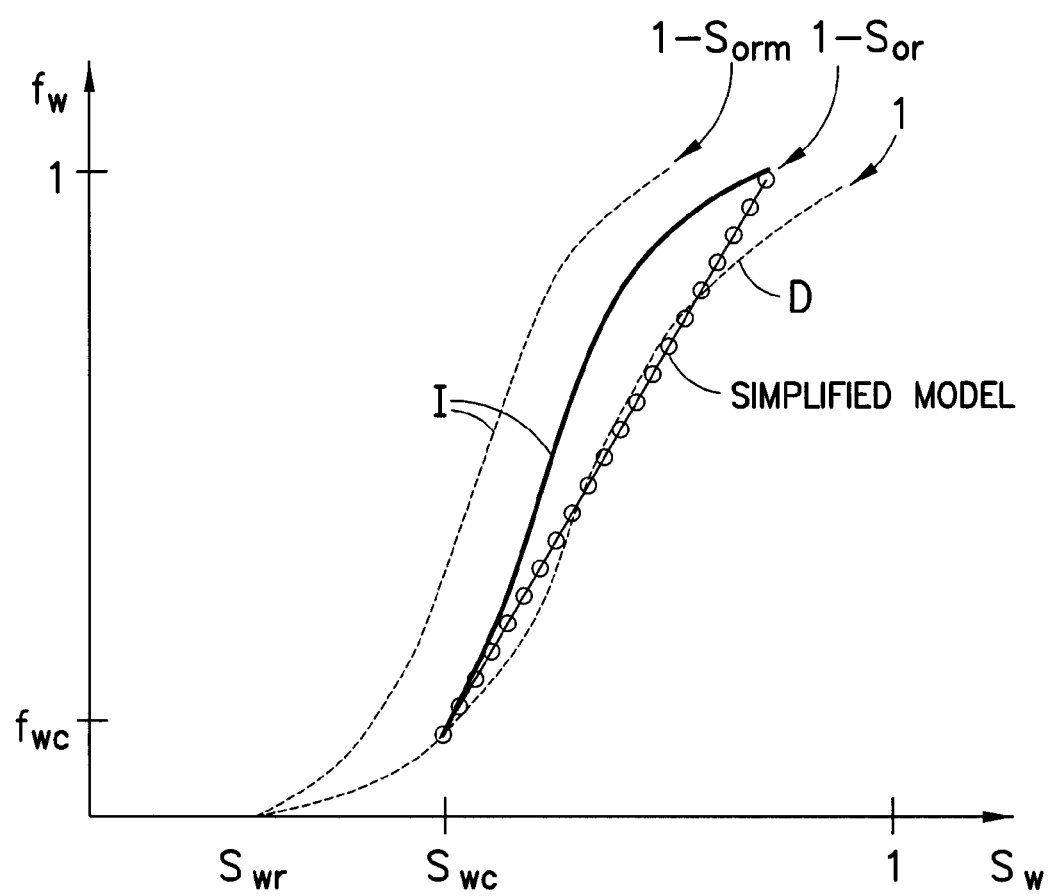
FIG. 2 is an example of a fractional fluid flow diagram.

Referring to FIG. 2, there is shown an example of a typical diagram of fractional flow versus saturation in a sandstone formation. The curve of FIG. 2 illustrates the fractional flow behavior in the rock (formation), and the effect of drainage and imbibition that occurred due to nature, or due to the invasion process. The point on the curve at $S_w=1$ and $f_w=1$ represents the original situation of millions of years ago with the rock pore spaces fully saturated with salt water (water saturation, $S_w=1$), and the fractional flow of water (defined as the ratio of the flow rate of water to the flow rate of total fluid) also unity ($f_w=1$). The portion of the curve labeled D is generally referred to as "drainage" and represents water being drained from some of the pore space volume as it is replaced by oil. If this process continued until water no longer flowed ($f_w=0$), the value of water saturation at such point would be commonly referred to as $S_{wr}$; i.e., the residual water saturation. The portion of the curve rising from this point, labeled I for "imbibition", represents water imbibing a successively greater fraction of the pore volume and replacing oil, as would occur as filtrate from water-based drilling fluid replaces oil. This curve terminates where all moveable oil has been flushed by water, at the point on the curve where $f_w=1$ (again, only water flows), and the water saturation is $S_w=1-S_{orm}$, where $S_{orm}$ is the maximum residual oil saturation.

As is well known, and evident from the curves of FIG. 2, the fractional flow characteristic exhibits hysteresis. In the description so far, it was assumed that drainage (D) proceeded all the way to $S_{wr}$. When, however, drainage is to an arbitrary connate water saturation, $S_{wc}$, the imbibition (I) follows a different path, and terminates (when only water flows) at $S_w=1-S_{or}$, where $S_{or}$ is the residual oil saturation. The residual oil saturation, $S_{or}$, is generally smaller than the maximum possible residual oil saturation, $S_{orm}$, that resulted from the earlier described situation where drainage proceeded all the way to $S_{wr}$.

In accordance with the present invention, the flow of filtrate and oil in a formation originally at a uniform connate saturation $S_{wc}$ is considered. The simultaneous movement of oleic and aqueous phases (termed oil and water here for convenience) are described by well-known mass conservation equations and two-phase Darcy equations. In accordance with one embodiment, the filtrate and the native water salinities are generally different thereby requiring an additional salt transport equation. One skilled in the art will recognize that it is possible to represent these in a compact matrix form $$\frac{\partial}{\partial \tau}\begin{pmatrix} S_w \\ \xi \end{pmatrix} + \begin{pmatrix} \frac{df_w(S_w)}{dS_w} & 0 \\ 0 & \frac{f_w(S_w)}{S_w} \end{pmatrix} \frac{\partial}{\partial \chi}\begin{pmatrix} S_w \\ \xi \end{pmatrix} = 0 \quad (1)$$

as set forth in Ramakrishnan et al., "Water Cut and Fractional Flow Logs from Array Induction Measurements", *SPE* 36503 (1996) which is hereby incorporated by reference herein in its entirety, where the water saturation is $S_w$ and the fractional flow of water is $f_w$, and $\xi$ is the dimensionless concentration defined as $$\xi = \frac{\psi - \psi_c}{\psi_m - \psi_c} \quad (2)$$

where $\psi$ is the volume fraction of salt saturated solution in the aqueous phase. The subscripts c and m in equation (2) imply connate and mud filtrate conditions respectively. The independent variables in equation (1) are $\tau$ and $\chi$, the dimensionless time and distance which are defined according to $$\tau = \frac{\int_0^t q(v)dv}{\pi r_w^2 \phi} \quad (3)$$

and $$\chi = \frac{r^2 - r_w^2}{r_w^2} \quad (4)$$

where t is the time at which the solution for $S_w$ and $\xi$ are desired, q is the filtrate loss per unit depth as a function of time, $r_w$ is the wellbore radius and $\Phi$ is the porosity.

Given the above, the solution to equation (1) is seen to be independent of the filtrate loss history q(t) and depends only on the cumulative loss:

$$Q = \int_0^t q(v)dv. \quad (5)$$

This result (i.e., being independent of the filtrate loss history q(t)) is a great advantage since quantifying the actual filtrate loss history is difficult or virtually impossible given the number of trips made, and the complicated nature of dynamic and static filtration. Thus, in accordance with the present embodiment, all of the aforementioned unknown aspects of filtration are represented by one parameter Q; the filtrate lost at the time of logging.

As set forth in previously incorporated U.S. Pat. No. 5,497,321 and in T. S. Ramakrishnan and Wilkinson, "Water Cut and Fractional Flow Logs from Array Induction Measurements", *SPE* 36503, (1996), it is possible to invert for $f_w(S_w)$ and Q from a single resistivity profile arising out of invasion. The inversion for $f_w(S_w)$ is carried out in terms of parameters in the relative permeability model of Ramakrishnan and Wasan, "Effect of Capillary Number on the Relative Permeability Function for Two-Phase Flow in Porous Media", *Powder Technology*, (1986), hereby incorporated by reference herein in its entirety. These parameters are the residual water saturation $S_{wr}$, the maximum residual oil saturation $S_{orm}$, the connate water saturation $S_{wc}$, and the pore size distribution index $\lambda$. In principle, it should be possible to invert for all of the above-mentioned quantities and Q. In practice, however, $\lambda$ is not generally invertible due to large variances associated with its estimate. Thus, in a preferred embodiment, whenever $\lambda$ inversion is ill-posed, it will be assumed that its value is 2.

In contrast to previously incorporated U.S. Pat. No. 5,497,321, the present invention sets forth a method, system and apparatus for combining data obtained at various stages of filtrate invasion through time lapse measurement. While the present invention is described with reference to an LWD environment, it will be appreciated that the described environment is solely for the purposes of clarity and is not intended to limit the scope of the present invention.

When a logging tool such as shown in FIG. 1 is used to collect data, each pass of the tool gives a set of responses corresponding to a cumulative filtrate loss, say $Q_i$, where i is the pass number, ranging from 1 to N. If one considers an M array measurement for each pass, the total number of data points become NM. In one aspect of the present invention, N could be arbitrarily large. For example, N could be as high as 20. Using the present invention, all of the NM measurements may be united with a common physics model. At a given well depth, the petrophysical parameters $S_{wr}$, $S_{orm}$, and $\lambda$ will not change, since these are intrinsic formation properties. Similarly the initial condition $S_{wc}$ is a fixed quantity, independent of invasion. Thus the number of unknowns for each pass increases by 1, namely $Q_i$ for that pass.

At first glance it might appear that the conductivity logs at each $Q_i$ provide independent information. Thus, one might be led to conclude that more parameters may be inverted than the ones listed above. Numerical experiments conducted in this regard find this to be generally untrue. As a result, utilizing time-lapsed data permits a better quality of inversion by (i) increasing the number of data points in relation to the number of unknowns and (ii) by providing information at different invasion amounts; i.e., the error bars for the inverted parameters will decrease. It is beneficial to provide information at different invasion amounts, as the effect of invasion on resistivity logs is dependent on the depth of invasion and the depth of investigation. As an example, data obtained at a single point in time can suffer from lack of resolution when the invasion is deep and all the logs read about the same value. In the case of data obtained at many different times, even if the data obtained from a late pass do not have the requisite separations, the data obtained from an early pass is likely to have the requisite separations, thus ensuring a robust inversion.

Figure 3:
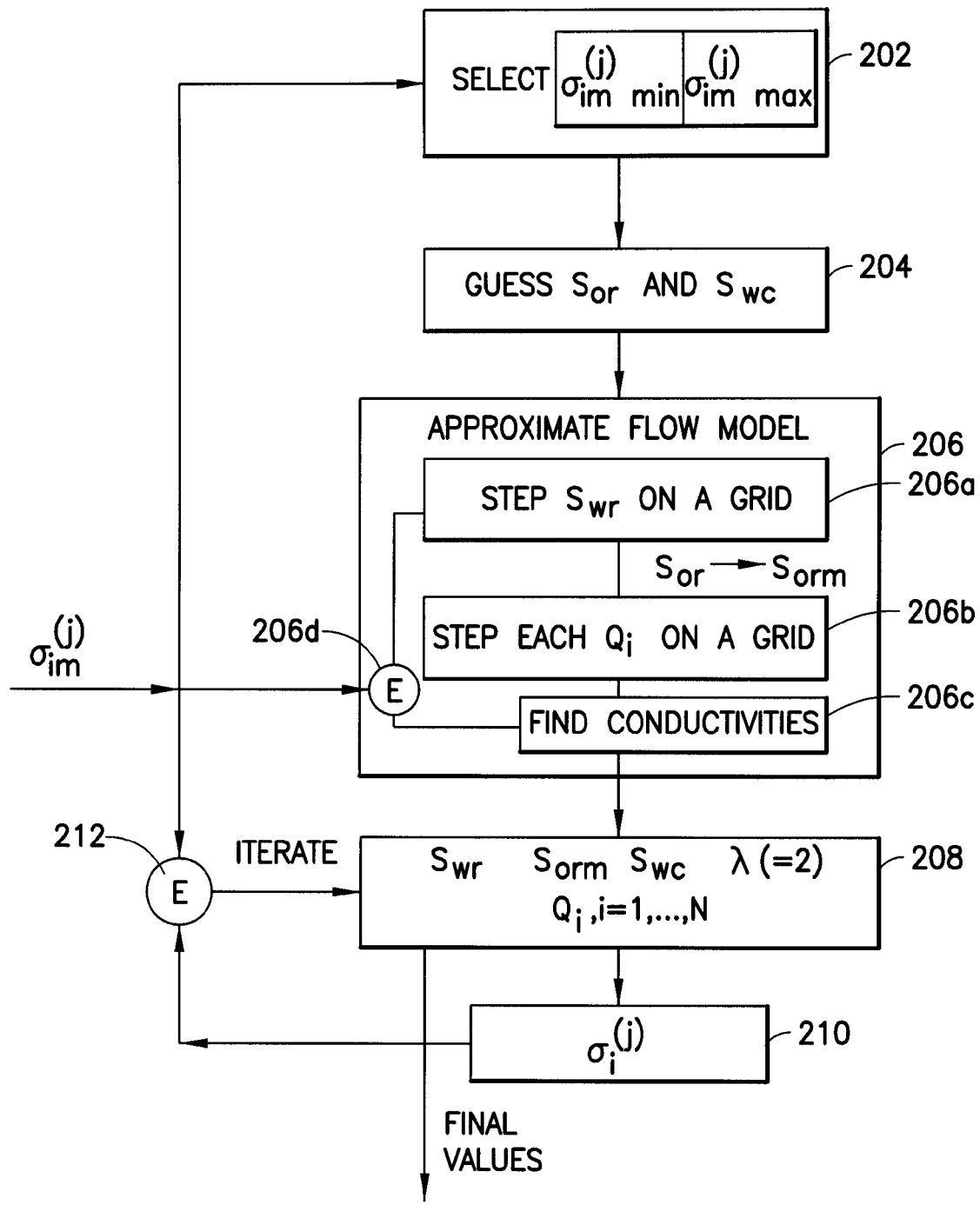
FIG. 3 is a flow chart of a method of the invention.

According to one embodiment of the invention, data obtained from the tool 42 of FIG. 1 are processed according to the flow chart of FIG. 3. More particularly, let the subscript i denote the i'th pass of logging with a total of N passes. Let the channels (depths of investigation) in each pass be denoted with a superscript: (j), ($0 \leq j \leq M$). Thus $\sigma_i^{(j)}$ denotes j'th conductivity channel, in the i'th pass. An additional subscript m denotes measured values. For each of the passes of the tool through the borehole, the problem is parameterised as set forth in previously incorporated Ramakrishnan and Wilkinson, SPE 36503 (1996). Thus, the fractional flow curve $f_w(S_w)$ is described completely by the parameters $S_{wr}$, $S_{orm}$, $S_{wc}$, and $\lambda$. For the i'th pass, the unknown filtrate loss is $Q_i$. It is assumed that information regarding petrophysics such as the conductivity-saturation equation is independently known and that parameters such as the porosity, wellbore radius, viscosity ratio and water conductivities are available from logs or fluid samples.

As seen in FIG. 3, the first step 202 is to evaluate the shallowest ($\sigma_{im}^{(0)}$) and the deepest log of measured conductivity values ($\sigma_{im}^{(M)}$) of the M+1 measurements in each pass for each borehole depth. In one embodiment, among the N values in each of these sets at a given borehole depth, the largest shallow conductivity value and the smallest deep conductivity value for the borehole depth being analysed are chosen. In another embodiment, for each borehole depth being analysed, the shallowest conductivity of the final run and the deepest conductivity of the first run are chosen. Generally, these values will correspond to the values of the first embodiment, although differences may arise for exceptional cases such as deep invasion combined with excessively fresh water filtrate in a water zone. Thus, in a third embodiment, for each borehole depth being analysed, selection is accomplished using both the first and second embodiments, and the choice that produces the least possible error between the measurements and the model values are used as discussed below. For purposes of simplicity of description, however, FIG. 3 will be discussed on the assumption that the largest shallow conductivity value and smallest deep conductivity value are utilized. Thus, the largest shallow conductivity value is used at step 204 to compute an estimated or starting residual oil saturation value $S_{or}$ for that borehole depth according to $$\max[\sigma_{im}^{0}] = \sigma_f \phi^m (1 - S_{or})^n \tag{6}$$

where $\sigma_f$ is the conductivity of invading water or the mud filtrate (typically a measured value), $\phi$ is the porosity, and the superscripts m and n are the cementation and the saturation exponents. Alternative models which include the effect of clay conduction such as the Waxman-Smits model or dual water model are also usable, provided the additional parameters such as cation exchange capacity are known. At step 204 the smallest deep conductivity value is used to obtain an estimated or starting connate water saturation value $S_{wc}$ for that borehole depth according to $$\min[\sigma_{im}^{M}] = \sigma_{wc} \phi^m (S_{wc})^n \tag{7}$$

Here $\sigma_{wc}$ is the conductivity of the formation water. The residual oil saturation value $S_{or}$ is the residual oil for the imbibition cycle starting at $S_{wc}$ of interest and is in general lower than $S_{orm}$.

At 206, using the starting values of $S_{or}$ and $S_{wc}$, a multidimensional global search for good starting guesses of the residual water saturation $S_{wr}$ and the drilling mud infiltrations (filtrate losses) $Q_i$ is conducted. More particularly, in one embodiment, a stepping grid (e.g., a DO loop) for $S_{wr}$ running from, e.g., 0 to e.g., $S_{wc}$ or some fraction thereof in desired increments is established at 206a as an outer loop. For each value of $S_{wr}$ in the grid, a stepping grid (e.g., a DO loop) in $Q_i$ ranging between some $Q_{min}$ and $Q_{max}$ in desired increments ($\Delta Q$) is investigated at 206b as an inner loop. Thus, given the starting $S_{or}$ value based on the largest shallow conductivity value, and the starting $S_{wc}$ value based on the smallest deep conductivity value, a normalized value $S_{or}^*$ and a normalized $S_{wc}^*$ can be computed according to:

$$S_{or}^* = \frac{S_{or}}{1 - S_{wr}} \tag{8}$$

and $$S_{wc}^* = \frac{S_{wc} - S_{wr}}{1 - S_{wr}} \tag{9}$$

Using $S_{or}^*$ and $S_{wc}^*$ a normalized maximum residual oil saturation value $S_{orm}^*$ can be found according to $$S_{or}^* = \frac{1 - S_{wc}^*}{1 + \left(\frac{1}{S_{orm}^*} - 1\right)(1 - S_{wc}^*)} \tag{10}$$

$S_{orm}$ may be found from $S_{orm}^*$, according to $$S_{orm}^* = \frac{S_{orm}}{1 - S_{wr}} \tag{11}$$

With starting estimates for all the fractional flow parameters calculated, a conductivity profile $\sigma_t(r)$ can be calculated for each of the filtrate loss values $Q_i$ in the grid by utilizing a two-phase flow model. In one embodiment, the two-phase flow model is based on a complex fractional flow model as in FIG. 2. In a presently preferred embodiment, however, the flow model is simplified and assumes a straight line fractional flow "curve" connecting points ($f(S_{we})$, $S_{wc}$)) and ($1$, $1-S_{or}$) of FIG. 2 (as seen by the labeled line having circles of FIG. 2). The corresponding conductivity logs for each channel j and for each pass i may then be calculated at 206c using $$\sigma_i^{(j)} = \int_0^\infty A^j(r) \sigma_t(r) dr \tag{12}$$

where $A^j(r)$ are the radial response functions for a specific tool configuration which generally depend on other processing parameters such as background conductivity. The calculation of equation (10) is rapid when the fractional flow curve is replaced by a straight line and is therefore useful in carrying out a search algorithm. The calculated conductivities are then compared at 206d to the conductivities $\sigma_{im}^{\ j}$ measured by the borehole tool (where subscript m indicates a measured value), and errors in each pass i are calculated according to $$E_i = \sum_{j=0}^{M} \left( \frac{\sigma_i^{(j)} - \sigma_{im}^{(j)}}{\sigma_{im}^{(j)}} \right)^2. \tag{13}$$

Thus, in order to find a first set of initial values for $S_{wr}$ (and initial values for $Q_i$), two loops are set up. In the described embodiment, $S_{wr}$ is used in an outer loop and $Q_i$ is used in an inner loop (although in another embodiment the two could be reversed), so $S_{wr}$ is fixed while $Q_i$ is varied. For each of the N passes in which $Q_i$ is varied, the filtrate loss value that minimizes the error $E_i = E_{i\ min}$ is selected. To keep the algorithm sufficiently general and unbiased, according to one embodiment, no magnitude based ordering among the filtrate losses $Q_i$ is imposed during the search.

After running through the N iterations to find an $E_{i\ min}$ which corresponds to a particular filtrate loss value, the value for the outer loop $S_{wr}$ is changed, and the procedure continues by running through the inner loop to find filtrate loss values that minimize the error for the new outer loop $S_{wr}$ value. After stepping through all of the $S_{wr}$ values, a total error (over all i passes) is then calculated as a sum of the minimized errors $E_{i\ min}$ according to $$E = \sum_{i=1}^{N} E_{i\min} \tag{14}$$

for each of the $S_{wr}$ values. The value of $S_{wr}$ that has the least value of E is chosen as the starting value.

According to one embodiment, the errors as defined by Equation (13) and then summed in equation (14) may be appropriately changed (i.e., defined differently) to have weights different from the reciprocal of the square of the measured conductivities based on the noise statistics gathered by suitable testing of the tool. Thus, the weighting would be related to the inverse of the variance of the measurement. Regardless of the manner in which error is defined, the aim of the search program is to pick the set of $S_{wr}$ and the N values of $Q_i$ which minimize the total error E for each borehole depth. Once this is done, the initialization of the formation parameters is complete; i.e., initial values for $S_{wr}$, $S_{wc}$, $S_{orm}$ have been selected. In addition, an initial N values of $Q_i$ have been selected.

With initial values for the formation parameters and $Q_i$ identified, the flow model utilizing the complete S-shaped fractional flow curve as shown in FIG. 2 and described in previously incorporated U.S. Pat. No. 5,497,321 and in Ramakrishnan et al., "Water Cut and Fractional Flow Logs from Array Induction Measurements", *SPE* 36503, (1996), is applied at step 208 to compute conductivities $\sigma_i^{(j)}$ (step 210) for a given combination of $S_{wr}$, $S_{orm}$, $S_{wc}$ and $Q_i$ values. The computed conductivities are compared at step 312 to the conductivities $\sigma_{im}^{(j)}$ measured by the tool. A multidimensional iterative algorithm (e.g., a nonlinear least squares algorithm) is then utilized to modify (fine tune) formation parameter values $S_{wr}$, $S_{orm}$, $S_{wc}$ and $Q_i$ values by totaling the errors for each combination of parameter values and $Q_i$ values over multiple passes i according to $$E = \sum_{i=1}^{N} E_i \tag{13}$$

and finding a minimal error so as to find an optimal (final) solution for the parameter values and $Q_i$ values for each depth of the borehole.

Figure 4A:
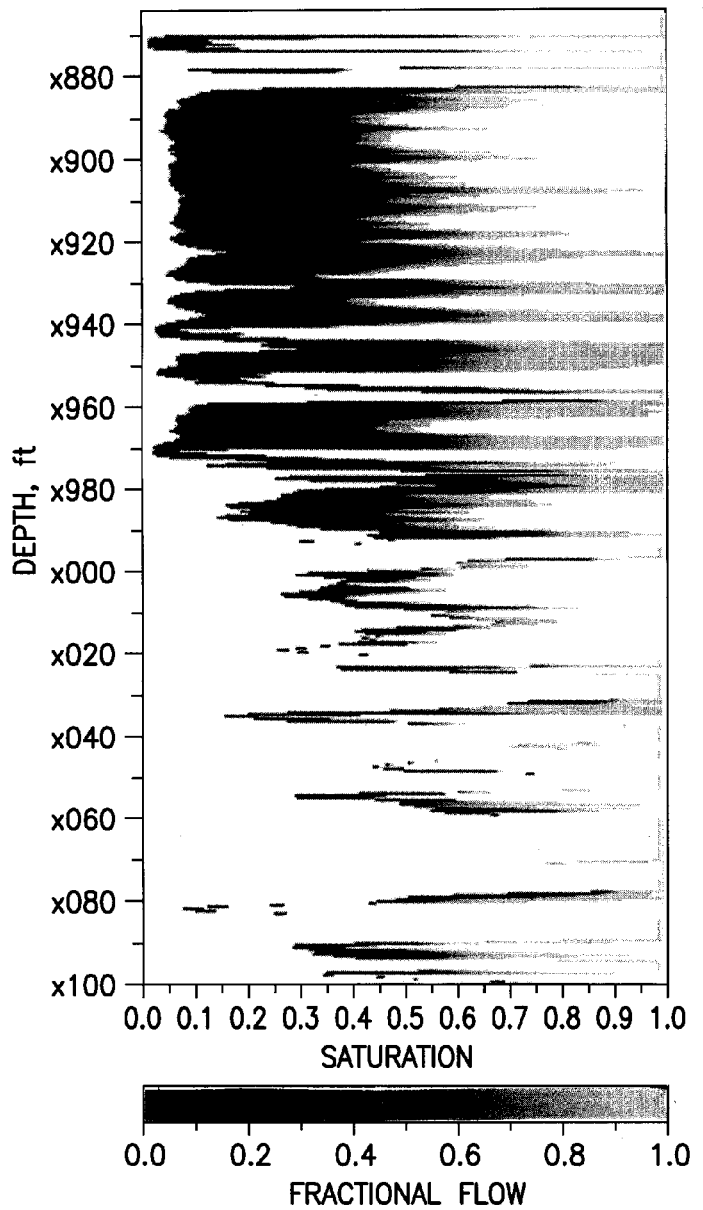
FIG. 4A is a sample log generated using well data showing saturation and fractional flow.
Figure 4B:
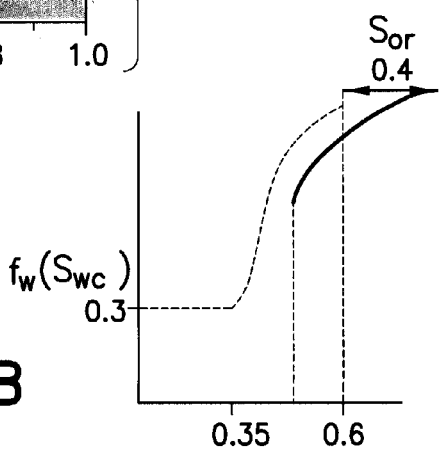
FIG. 4B is a fractional flow curve at a depth identified in FIG. 4.
Figure 5:
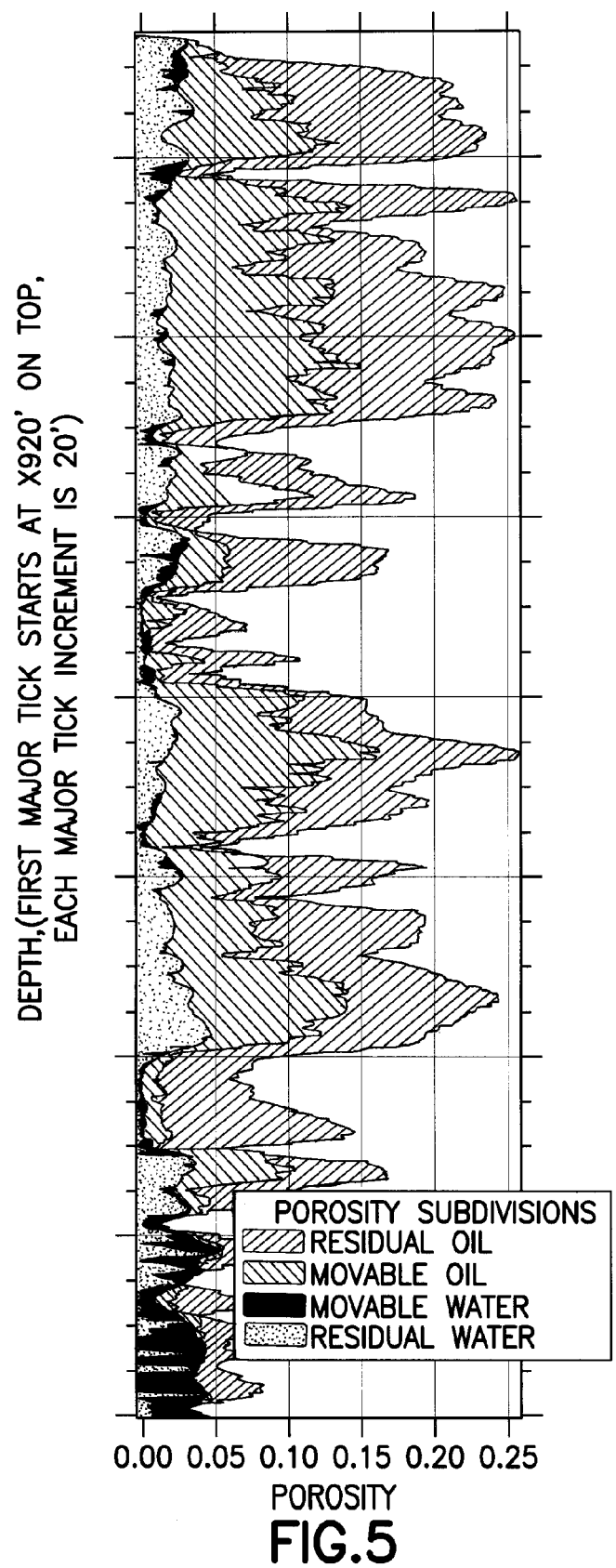
FIG. 5 is a sample plot of residual oil and water and movable oil and water porosity subdivisions over a borehole length.
Figure 6:
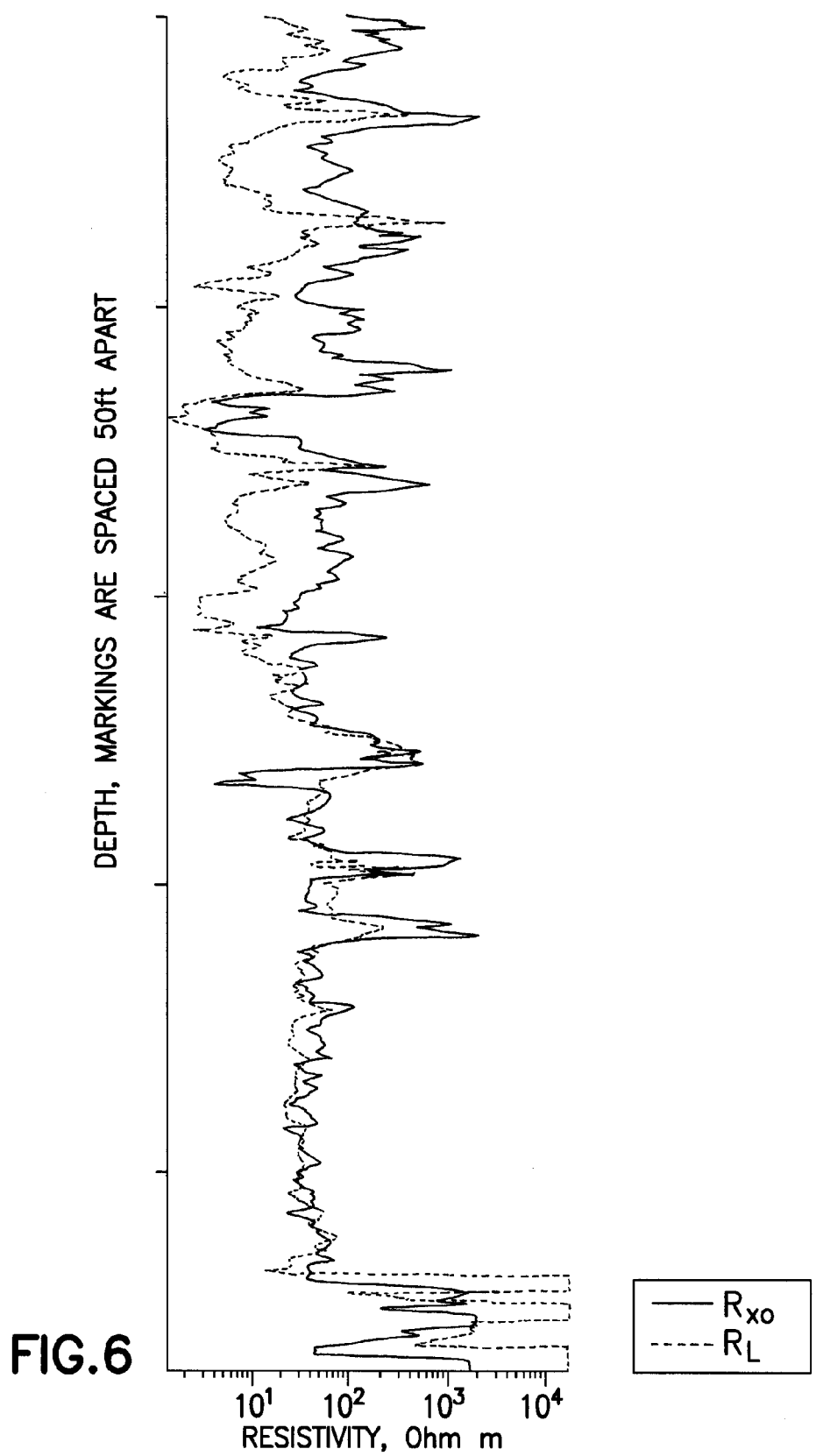
FIG. 6 is a sample log of formation resistivities in invaded and uninvaded regions of a borehole.

Once final determinations for $S_{wr}$, $S_{orm}$, and $S_{wc}$ are obtained, fractional flow curves and porosity partitioning into movable and residual saturations can be generated. Fractional flow and water and/or oil saturation can be represented as logs such as shown in FIG. 4, and also as shown in previously incorporated Ramakrishnan and Wilkinson, "Water Cut and Fractional Flow Logs from Array Induction Measurements" *SPE* 36503 (1996). The fractional flow curve at each depth (FIG. 4a) allows one skilled in the art to partition the oil saturation into residual and movable oil as seen in FIG. 5 The multiphase mobility in terms of relative permeabilities may also be generated from the inverted parameters. In addition, a log of the formation resistivity in the invaded and uninvaded regions can be generated as seen in FIG. 6, e.g., using the Archie model, according to $$\sigma_t = \sigma_{wc} \phi^m S_{wc}^{\ n} \tag{15}$$

for the uninvaded region, where $\sigma_t$ is the far field formation ("true") conductivity, and $$\sigma_{xo} = \sigma_f \phi^m (1 - S_{or})^n \tag{16}$$

for the invaded region, where $\sigma_{xo}$ is the formation conductivity at the borehole wall after invasion.

Figure 7:
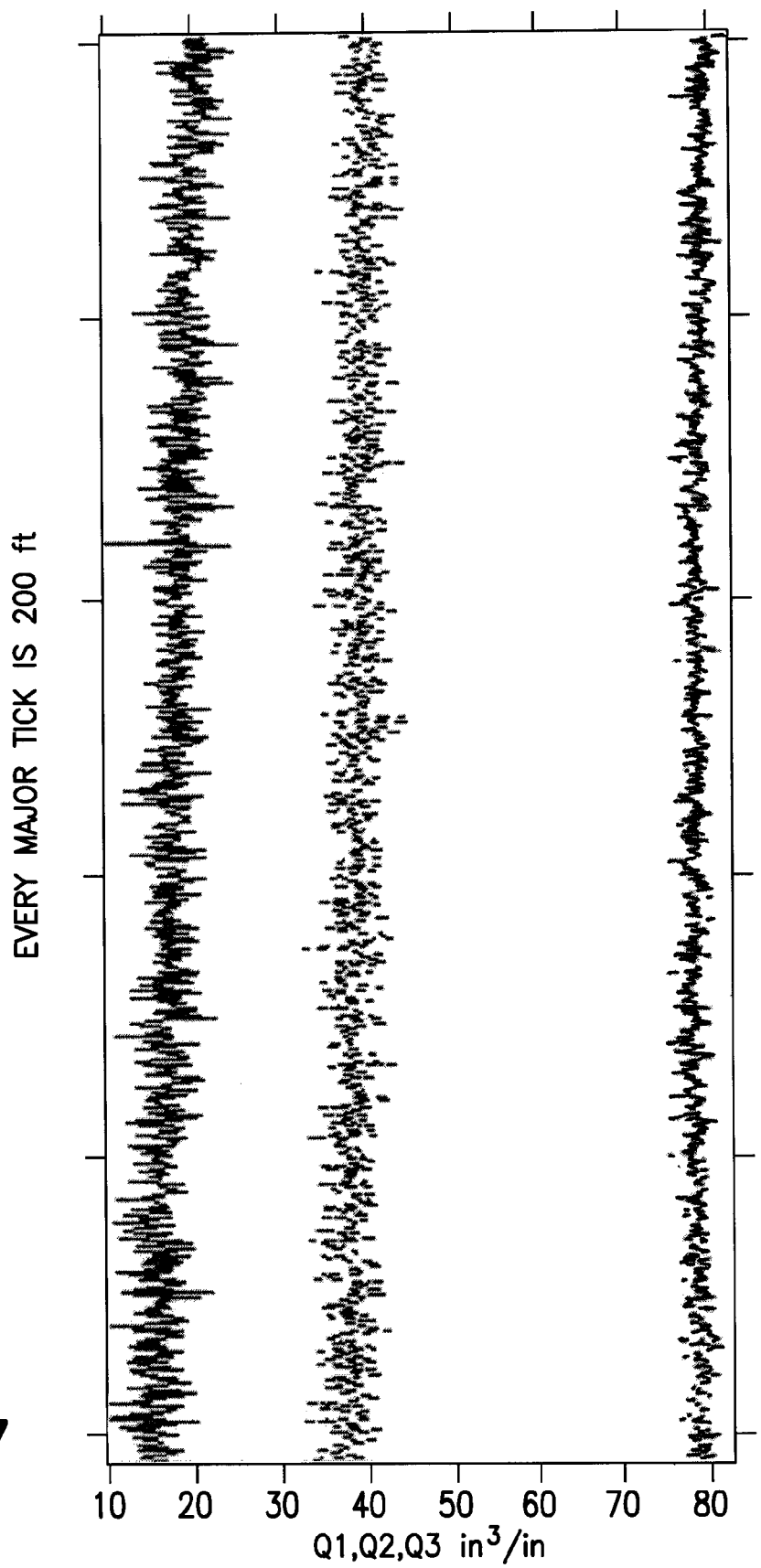
FIG. 7 is a sample log showing infiltration loss over time.

In fact, all the advantages of single pass inversion described in previously incorporated U.S. Pat. No. 5,497,321 are readily applicable according to the invention, and in addition, the accuracy of the results are considerably improved because of the time-lapse data. Furthermore, one or more logs of fluid filtrate loss (filtration into the formation) over time for each depth can be generated using the $Q_i$ values such as the made-up example shown in FIG. 7. The log(s) can be provided on a display apparatus or on paper(s).

There have been described and illustrated herein embodiments of a method, apparatus and system for analyzing time lapse resistivity data. While particular embodiments of the invention have been described, it is not intended that the invention be limited thereto, as it is intended that the invention be as broad in scope as the art will allow and that the specification be read likewise. Thus, while the use of particular resistivity tools have been disclosed, it will be appreciated that other tools capable of obtaining resistivity data at different radial depths into the formation could be utilized. In addition, while a particular search algorithm for conducting a global search for initial estimated values of $S_{wr}$ and $Q_i$ has been disclosed which utilizes an approximate flow model, it will be understood that other search algorithms can be used. For example, and not by way of limitation, the search algorithm could utilize a more complete flow model. It will therefore be appreciated that yet other modifications could be made to the provided invention without deviating from its spirit and scope as claimed.

What is claimed is:

1. A method of producing a log of a characteristic of a formation surrounding a borehole, comprising:
   a) moving a resistivity logging tool through the borehole a plurality of times to obtain each time resistivity measurements at a plurality of radial depths of investigation for a plurality of borehole distances;
   b) utilizing said resistivity measurements, generating starting estimates of residual oil saturation $S_{or}$ and connate water saturation $S_{wc}$ for each of said plurality of borehole distances;
   c) utilizing said starting estimates and said resistivity measurements, conducting an initial global multidimensional search for starting values of residual water saturation $S_{wr}$ and filtrate loss quantities $Q_i$ for each of said plurality of borehole distances;
   d) utilizing said starting values of residual water saturation, finding starting values for maximum residual oil saturation $S_{orm}$ at each of said plurality of borehole distances;
   e) using said starting values of connate water saturation $S_{wc}$, said starting values of residual water saturation $S_{wr}$, said starting values of maximum residual oil saturation $S_{orm}$, said starting values of filtrate loss quantities $Q_i$, i= 1, ... N for each of said plurality of borehole distances, and a first flow model relating $S_{wr}$, $S_{wc}$, $S_{orm}$ and $Q_i$ to resistivity, generating first resistivity estimates at different radial depths into the formation,
      (i) comparing said resistivity estimates generated by said first flow model to said resistivity measurements, and
      (ii) based on said comparing, iteratively modifying at least one of said starting values, generating updated resistivity estimates at said different radial depths into the formation utilizing said modified starting values, and comparing resulting updated estimates to the actual measurements to make determinations of at least one formation parameter; and
   f) displaying an indication of a value of said at least one formation parameter as a log over borehole distance.

2. A method according to claim 1, wherein:
said plurality of radial depths includes a shallowest radial depth and a deepest radial depth, and said generating starting estimates of residual oil saturation $S_{or}$ comprises, for each of said plurality of borehole distances of interest, finding a largest conductivity value of a plurality of conductivity values for said shallowest radial depth in order to compute said starting estimates of residual oil saturation.

3. A method according to claim 2, wherein:
said generating starting estimates of connate water saturation $S_{wc}$ comprises, for each of said plurality of borehole distances of interest, finding a smallest conductivity value of a plurality of conductivity values for said deepest radial depth in order to find said connate water saturation.

4. A method according to claim 1, wherein:
said plurality of radial depths includes a shallowest radial depth and a deepest radial depth, and said generating starting estimates of residual oil saturation $S_{or}$ and connate water saturation $S_{wc}$ comprises utilizing the shallowest conductivity of a final run and the deepest conductivity of a first run of said logging tool through the borehole.

5. A method according to claim 1, wherein:
said conducting an initial global multidimensional search comprises iteratively stepping values of water saturation and filtrate loss quantities on grids, and applying said values of water saturation and filtrate loss quantities to a second flow model relating $S_{wr}$, $S_{wc}$, $S_{orm}$ and $Q_i$ to resistivity, and comparing resulting second flow model-generated resistivity estimates to said resistivity measurements to find a minimum error.

6. A method according to claim 5, wherein:
said second flow model treats curves on plots of fractional flow versus water saturation as straight lines.

7. A method according to claim 1, wherein:
said iteratively modifying at least one of said starting values comprises iteratively modifying a plurality of said starting values.

8. A method according to claim 1, wherein:
said at least one formation parameter comprises fractional flow.

9. A method according to claim 1, wherein:
said at least one formation parameter comprises at least one of water saturation and oil saturation.

10. A method according to claim 1, wherein:
said at least one formation parameter comprises at least one of residual oil, movable oil, residual water, and movable water.

11. A method according to claim 1, wherein:
said at least one formation parameter comprises at least one of formation resistivity in an invaded region of the formation and formation resistivity in an uninvaded region of the formation.

12. A method according to claim 1, further comprising:
displaying filtrate loss quantities as a function of time at at least one distance in said formation.

13. A method according to claim 1, wherein:
said resistivity logging tool is coupled to a drilling tool, and said moving said resistivity logging tool comprises tripping said drilling tool into and out of the borehole a plurality of times.

14. A method of producing a log of a characteristic of a formation surrounding a borehole, comprising:
   a) moving a resistivity logging tool through the borehole a plurality of times to obtain time lapsed resistivity measurements at a plurality of radial depths of investigation for a plurality of borehole distances;
   b) utilizing a flow model of the formation which relates a plurality of parameters of the formation to the formation resistivity in order to generate estimates of formation resistivities at said plurality of radial depths at each of said plurality of borehole distances;
   c) comparing said estimates to said time lapsed resistivity measurements;
   d) based on said comparing, iteratively modifying and generating updated resistivity estimates at said different radial depths into the formation, and comparing resulting updated estimates to the actual measurements to make determinations of at least one formation parameter; and
   e) displaying an indication of a value of said at least one of said plurality of parameters of the formation as a log over borehole distance.

15. A method according to claim 14, wherein:
said flow model includes filtrate loss as a parameter, and said method further comprises displaying filtrate loss quantities as a function of time at at least one distance in said formation.

16. A method according to claim 14, wherein:
said at least one formation parameter comprises at least one of water saturation and oil saturation.

17. A method according to claim 14, wherein:
said at least one formation parameter comprises at least one of residual oil, movable oil, residual water, and movable water.

18. A method according to claim 14, wherein:
said at least one formation parameter comprises at least one of formation resistivity in an invaded region of the formation and formation resistivity in an uninvaded region of the formation.

19. A system for producing a log of a characteristic of a formation surrounding a borehole, comprising:
   a) a resistivity logging while drilling tool which is moved through the borehole a plurality of times, said resistivity logging while drilling tool includes means for obtaining each time said resistivity logging tool is moved through the borehole resistivity measurements at a plurality of radial depths of investigation for a plurality of borehole distances;
   b) processing means for
      (i) utilizing said resisitivity measurements, generating starting estimates of residual oil saturation $S_{or}$ and connate water saturation $S_{wc}$ for each of said plurality of borehole distances,
      (ii) utilizing said starting estimates and said resistivity measurements, conducting an initial global multidimensional search for starting values of residual water saturation $S_{wr}$ and filtrate loss quantities $Q_i$ for each of said plurality of borehole distances,
      (iii) utilizing said starting values of residual water saturation, finding starting values for maximum residual oil saturation $S_{orm}$ at each of said plurality of borehole distances;
      (iv) using said starting values of connate water saturation $S_{wc}$, said starting values of residual water saturation $S_{wr}$, said starting values of maximum residual oil saturation $S_{orm}$ said starting values of filtrate loss quantities $Q_i$, i=1, . . . N for each of said plurality of borehole distances, and a first flow model relating $S_{wr}$, $S_{wc}$, $S_{orm}$ and $Q_i$ to resistivity, generating first resistivity estimates at different radial depths into the formation,
      comparing said resistivity estimates generated by said first flow model to said resistivity measurements, and
      based on said comparing, iteratively modifying at least one of said starting values, generating updated resistivity estimates at said different radial depths into the formation utilizing said modified starting values, and comparing resulting updated estimates to the actual measurements to make determinations of at least one formation parameter; and
   c) display means coupled to said processing means for displaying an indication of a value of said at least one formation parameter as a log over borehole distance.

20. A system according to claim 19, wherein:
said display means displays filtrate loss quantities as a function of time at at least one distance in said formation.

21. A system according to claim 19, wherein:
said at least one formation parameter comprises at least one of water saturation and oil saturation.

\* \* \* \* \*